United States Patent [19]
Hanson

[11] Patent Number: 5,711,666
[45] Date of Patent: Jan. 27, 1998

[54] SELF-LIGATING ORTHODONTIC BRACKETS

[76] Inventor: G. Herbert Hanson, 57 Augusta St., Hamiliton, Canada, L8N 1P8

[21] Appl. No.: 734,833

[22] Filed: Oct. 22, 1996

[51] Int. Cl.$^6$ .................................................. A61C 7/28
[52] U.S. Cl. .................................................... 433/11
[58] Field of Search .......................... 433/10, 11, 13, 433/14, 17

[56] References Cited

U.S. PATENT DOCUMENTS

| | | | |
|---|---|---|---|
| 3,043,006 | 7/1962 | Wallshein | 433/11 |
| 3,076,265 | 2/1963 | Moore | 433/11 |
| 3,218,713 | 11/1965 | Wallshein | 433/11 |
| 3,772,787 | 11/1973 | Hanson . | |
| 4,248,588 | 2/1981 | Hanson | 433/11 |
| 4,492,573 | 1/1985 | Hanson | 433/11 |
| 4,698,017 | 10/1987 | Hanson | 433/11 |
| 5,224,858 | 7/1993 | Hanson | 433/10 |
| 5,288,229 | 2/1994 | Huff et al. | 433/17 |
| 5,344,315 | 9/1994 | Hanson | 433/20 |

Primary Examiner—Cary E. O'Connor
Attorney, Agent, or Firm—Rogers & Scott

[57] ABSTRACT

An orthodontic bracket comprises a bracket body with a mesial distal extending arch wire slot and a ligating latch spring member having the form of a thin flat metal strip. The spring member comprises along its length, in the order stated, an anchor portion anchored in the bracket body, a flexing portion in which the majority of the flexing takes place, a ligating portion that closes the slot mouth and engages any arch wire therein, and a latching portion by which the spring member is latched to the bracket body. The spring member may comprise a biasing portion between the flexing and ligating portions at the slot occlusal surface, or between the ligating and latching portions at the slot gingival surface, this biasing portion being convex toward the slot lingual wall and protruding into the slot to press the arch wire into the respective slot wall junction for more precise control. The bracket body may be made as two mirror image parts which are laser welded together and between which the spring member is mounted. The latches between the spring member and the bracket body may comprise notches in the spring edges that are engaged by latch sears on the body, and two labially lingually spaced sears may be provided. Preferably the spring member is made of a nickel titanium shape memory alloy. The bracket body may have two pairs of tie wings for reception of an external ligature between which the spring member is disposed.

21 Claims, 7 Drawing Sheets

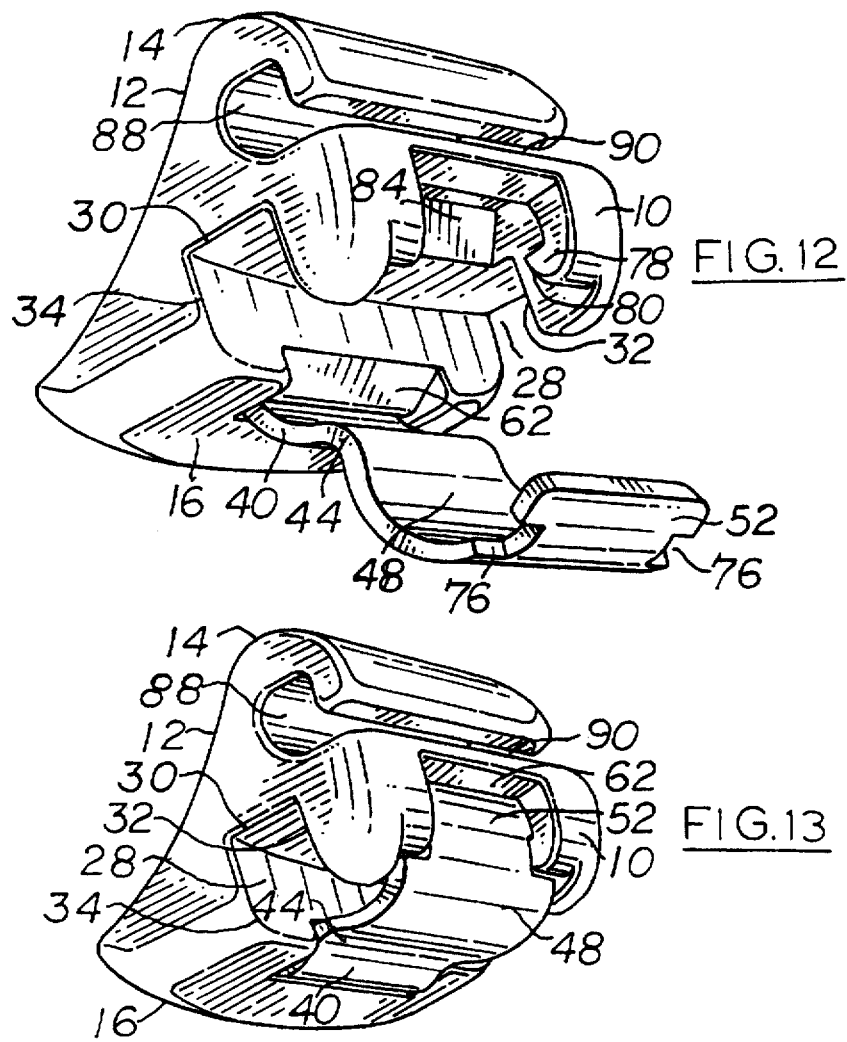
FIG. 12
FIG. 13
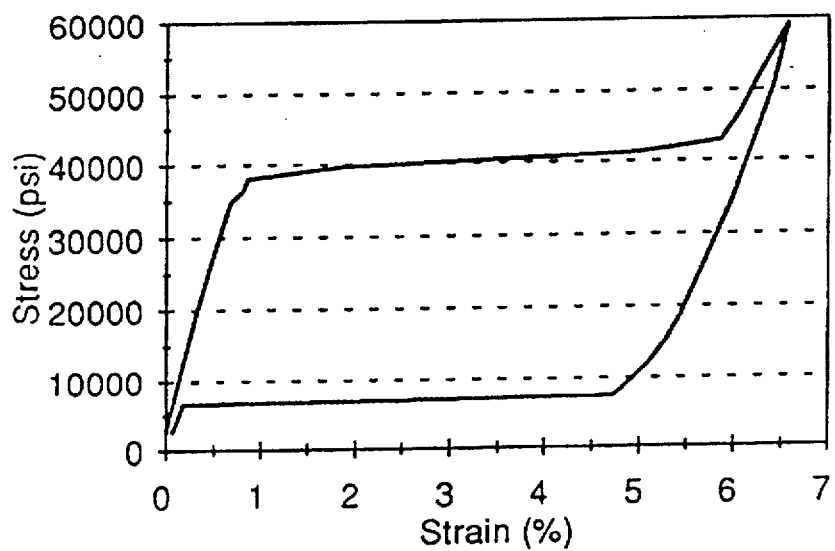
FIG. 14

SELF-LIGATING ORTHODONTIC BRACKETS

FIELD OF THE INVENTION

This invention is concerned with improvements in or relating to self-ligating orthodontic brackets, namely orthodontic brackets which comprise ligating spring means as a permanent part thereof.

REVIEW OF PRIOR ART

The majority of orthodontic procedures employ a plurality of brackets that are attached to respective teeth, increasingly by cementing them to the teeth, although in some circumstances they still may be attached to metal bands that embrace the respective teeth. Each bracket has a mesial distal extending slot therein, usually of rectangular cross section in a gingival occlusal plane, and the brackets are connected together using an arch wire, so called because it is preformed to an optimum arch shape corresponding to the desired conformation of the teeth at the conclusion of the procedure. Arch wires of progressively increasing stiffness and, depending on the type of tooth movement to be achieved, also of different cross section, are used one at a time, the wire being retained in the slots by ligating means of some kind. Initially the ligating means usually was a metal wire that was twisted about the bracket and the arch wire; subsequently as elastomeric materials were developed that could withstand the hostile environment of the human mouth elastomeric hoops or loops are increasingly commonly used. In another line of development each bracket comprises a permanently mounted self-ligating spring member; specific examples of such brackets are those disclosed and claimed in my U.S. Pat. Nos. 3,772,787; 4,248,588 and 4,492,573, and in my application Ser. No. 08/274,077, filed 12 Jul. 1994, the disclosures of which are incorporated herein by this reference. These brackets are currently in use in the Hanson SPEED System (Trade Mark) and have proven to be very successful.

There is a constant endeavour in orthodontics to provide brackets that are as small and as smooth exteriorly as possible, for cosmetic reasons to please the patient, and to reduce as much as possible the likelihood of rough contact between the brackets, the tongue and the adjacent mouth tissue, with consequent discomfort, and for hygienic reasons to reduce the number of areas in which food and dental plaque can accumulate. The orthodontist is interested in addition to use brackets that provide fast, precise and effective movement and attitude control of the teeth.

There is also increasing interest in the so-called lingual technique, in which the brackets are mounted on the lingual tooth surfaces, so that they and the wire are concealed from frontal view. Lingual procedures are more difficult to implement and a compromise is to use a lingual technique only for the upper arch, where the brackets and wire would otherwise be most visible, and a labial technique for the lower arch, where the brackets and wire usually are mostly hidden by the lower lip. Lingual and mixed lingual/labial procedures are of special interest to adult patients who are more concerned than children with appearance during the two-three year period required for a typical procedure. Small smooth brackets are needed particularly for the lingual location because of ready access by the tongue, and the natural tendency to use the tongue to explore any foreign object in the mouth. Attempts simply to reduce the size of existing brackets are not generally successful, at least partly because changes in scale affects size parameters in different ratios, e.g. areas decrease in square ratio while volumes decrease in cube ratio, with the result that it becomes increasingly difficult, especially with the tiny spring members required in self-ligating brackets, to find materials of the necessary properties. Examples of such small smooth exterior brackets suitable for lingual procedures are those described and claimed in my U.S. Pat. No. 4,698,017, issued 6 Oct. 1987, and my application Ser. No. 08/568,219, filed Jun. 12, 1995, the disclosures of which are incorporated herein by this reference.

The manufacture of orthodontic equipment is a mature industry, and the ongoing requirement to provide equipment that is efficient, economical and easy to use increasingly has the added requirement to be as inexpensive as possible, especially if orthodontists are to be persuaded to make the changes in their procedures that the adoption of new brackets usually entails.

SUMMARY OF THE INVENTION

It is a principal object of the invention therefore to provide new self-ligating brackets.

It is another principal object to provide new self-ligating brackets of small size and of smooth exterior contour, so as to make them specially suitable for use in lingual techniques.

It is a further object to provide such new self-ligating brackets requiring a minimum number of parts and in which the cost of their fabrication is minimized.

In accordance with the invention there is provided an orthodontic bracket comprising:

- a bracket body having labial, lingual, gingival, occlusal, mesial and distal surface portions, the body having therein a mesial distal extending arch wire slot having lingual, gingival, and occlusal surfaces and opening to the bracket lingual surface portion; and
- a ligating latch spring member having the form of a thin flat metal strip and comprising along its length in the order stated an anchor portion, a flexing portion, a ligating portion and a latching portion;
- wherein the anchor portion is retained by the bracket body to retain the spring member on the bracket body;
- the ligating and latching portions are movable by flexing of the flexing portion between a slot open position in which the slot opening is open for insertion of an arch wire into the slot, and a latched slot closed position in which the slot opening is closed by the ligating portion for retention thereby of an arch wire in the slot; and
- the spring member is latched in the slot closed position by latching engagement between the latching portion and the bracket body.

The spring member may comprise a biasing portion between the anchor and flexing portions at the slot occlusal surface, or instead between the ligating and latching portions a biasing portion at the slot gingival surface, the biasing portion being convex toward the slot lingual wall and protruding into the slot.

The spring member may have the anchor portion within a close fitting slot in the bracket body to retain the spring member on the bracket body and to prevent any movement of the anchor portion, so that flexing of the spring member upon movement between slot open and closed positions can only take place in the remainder of the spring member.

The shape of the spring member in the unstrained slot open position and its retention by the body may be such that in the slot open position it extends labially to provide a platform on which an arch wire can rest during the course of a procedure.

The bracket body may be provided between the arch wire slot and the gingival surface with a second mesial distal extending slot, the second slot having a mesial distal extending opening to the lingual surface of reduced gingival occlusal dimension through which an elastomeric orthodontic element can be introduced into the slot and will be retained therein.

The ligating portion may be concave toward the slot lingual wall. The spring member may be made of a shape memory metal, and preferably is made of a nickel titanium shape memory alloy.

The bracket body may have two pairs of tie wings for the reception and retention of an external ligature, the two wings of each pair extending gingivally and occlusally away from one another, the two pairs being spaced mesially distally from one another, and the spring member being disposed on the body between the tie wing pairs.

The bracket body may be made as two mirror image parts which butt one another at a junction, and between which the spring member is retained, the two body parts being fastened together at their junction.

The flexing portion may be of smaller width in the mesial distal direction than the anchor and ligating portions, whereby the flexibility of the flexing portion is greater than that of the anchor and ligating portions.

Means for latching the spring member to the bracket body may comprise two labially spaced pairs of latch sears, each pair of sears being alternatively engageable with a pair of mesially distally spaced latch notches in the edges of the spring member.

DESCRIPTION OF THE DRAWINGS

Particular preferred embodiments of the invention will now be described, by way of example, with reference to the accompanying diagrammatic drawings, wherein:

FIGS. 12 and 13 are perspective views of a wingless bracket of the invention intended particularly for lingual procedures and for attachment to upper canines and incisors, showing respectively the spring member in slot open and slot closed positions;

FIG. 14 is a stress strain diagram typical of shape memory metals, particularly nickel titanium shape memory alloys;

DESCRIPTION OF THE PREFERRED EMBODIMENTS

Figure 1:
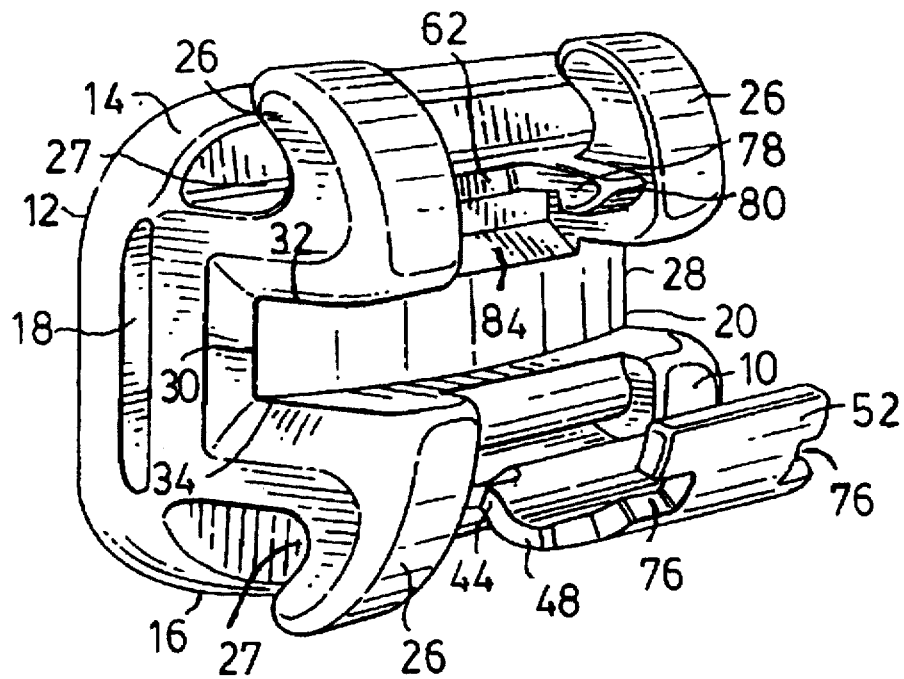
FIGS. 1 and 2 are perspective views from the mesial of a first embodiment which has the form of a double tie wing "siamese" bracket, as used in labial procedures, and with which additional ligatures can be used, showing the ligating latch spring member respectively in slot open and slot closed positions, and which has a spring member biasing portion at the slot occlusal surface.
Figure 2:
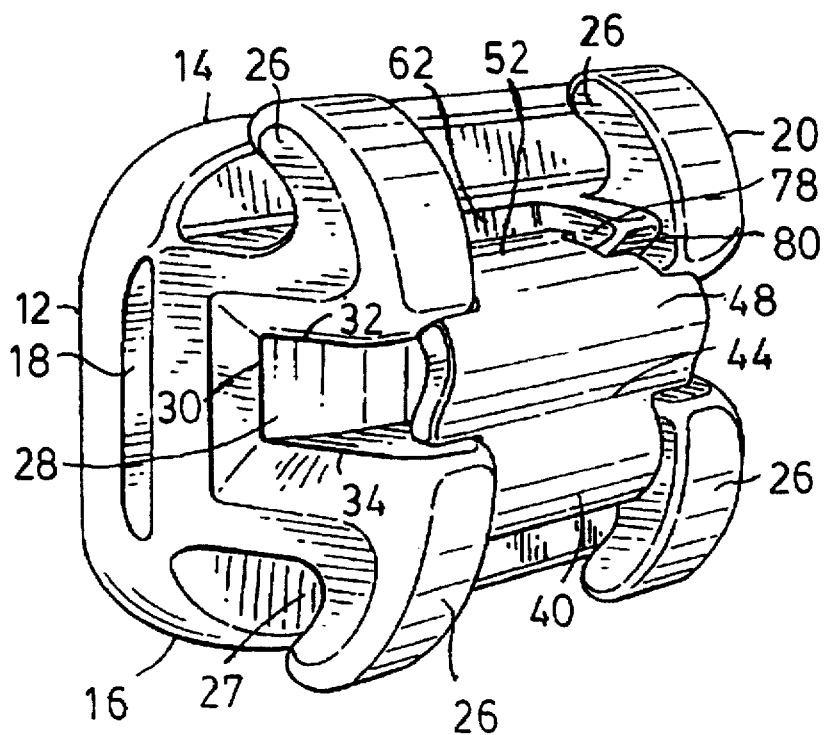

In this specification and the appended claims, for convenience in language the brackets and pans thereof are referred to, unless otherwise specified, as they would be used mounted in the upper arch region of a patient's mouth and employed in a labial procedure, even though the brackets may be used for either labial or lingual procedures, and certain of the brackets are intended particularly for lingual procedures. As applied to the bracket structure the labial and lingual direction designations are reversed between the two procedures, e.g. the bracket surface referred to as the labial surface in the labial procedure becomes the lingual surface in the lingual procedure, and vice versa, and the arch wire slot opens to the lingual and not the labial. Again for convenience in description the brackets are described as having specific named surfaces but, as will be apparent, smooth exterior contours can only be achieved by avoiding sharp edges and sharp edged junctions wherever possible, and the various surfaces therefore usually merge smoothly with one another without a definite junction between them being apparent.

Similar parts are given the same reference number in all the Figures of the drawings wherever this is appropriate.

The brackets of the invention as described and shown herein are intended for use with the so-called straight wire technique with which each bracket is attached to its respective tooth in an attitude such that, as the arch wire attempts to return to its preformed arch shape and to be straight as seen in a labial-lingual plane, the tooth is moved toward its desired optimized position and attitude. In order for the arch wire to be straight at the conclusion of the procedure the brackets for different teeth must accommodate for the very different inclinations of the tooth surfaces to which they are attached. There are two main methods by which this is done, either by suitable shaping of the bracket bases and of their base surfaces that contact the teeth surfaces, or by changing the inclination of the arch wire slots.

In the brackets shown herein all of the torque requirements (rotation about a mesial distal axis), angulation requirements (rotation about a labial lingual axis), and first order pre-adjustments, are obtained by suitable shaping of the bracket bases, particularly of the surface that engages the tooth surface, and by variation of the base thickness, so that when the teeth are in their optimum attitude and rotational position all of the slot surfaces engaged by the arch wire are aligned. The shape of the bases of the brackets shown in FIGS. 1–6, 10, 11, 15 and 16 make them suitable for attachment to an upper central incisor, while the base shape for the bracket of FIGS. 12, 13 and 17 make it suitable for an upper first central incisor. Shapes required for the other teeth will be apparent to those skilled in the art and need not be described in further detail herein.

The second method of slot inclination can also be used in the brackets of the invention, either alone or in combination with the first method. With some brackets the inclination of the slot may be so extreme that, for example, in a bracket fixed to the lingual surface of a central incisor no attempt is made to have the slot remain parallel with the labial lingual axis and instead it opens to the occlusal parallel to the gingival occlusal axis (as viewed from the mesial or distal), as will be seen in the brackets shown in FIGS. 12, 13 and 17; nevertheless such a bracket is within the scope of the language of the appended claims.

FIGS. 1 through 6, 15 and 16 show an externally ligatable form of the bracket of the invention that may be preferred by some orthodontists, even though the brackets are inherently self ligating. Thus, situations may arise in a procedure that require the use of an external ligature additional to, or even replacing, the ligature provided by the spring member, for example where initially a tooth is so grossly displaced that it is not possible to engage the arch wire in the slot or, if engaged, it is not possible to latch the spring member in the slot closed position without overstressing the spring member and/or the arch wire. Another consideration is that orthodontists who previously have only been using external ligatures in their procedures may be somewhat reluctant initially to adopt a bracket involving a completely new procedure, and which does not permit them at least the opportunity of using their established skills, and are reassured if provided with a self ligating bracket that also has provision for an external ligature. Such brackets are usually referred to as double tie wing or siamese tie wing brackets and in practice are only usable in labial procedures because of the projecting tie wings.

The bracket body has labial, lingual, gingival, occlusal, mesial and distal surfaces 10, 12, 14, 16, 18 and 20 respectively and is mounted on a tooth 22 (FIG. 17) by cementing it thereto, the lingual surface 12 being provided with two series of parallel intersecting grooves 24, the two series intersecting at a right angle to form a grid pattern (see FIGS. 3–5, 10, 11 and 16) that receives the cement. The body has two pairs of tie wings 26 for the reception and retention of an external ligature, such as an elastomeric loop ligature, in recesses 27 formed between the concave lingual surface of the tie wing and facing bracket body labial surface, the two wings of each pair extending gingivally and occlusally away from one another, and the two pairs being spaced mesially distally from one another. The tie wings can receive and anchor external wire tie wires, elastomeric hoop ligatures, and tension and compression members; the manner in which such orthodontic elements are used is well known to those skilled in the art and does not require explanation or illustration herein.

The body is provided with a mesial-distal extending labially opening arch wire slot 28, which in this embodiment is of rectangular transverse cross section in a gingival occlusal plane, the slot opening to the labial surface 10 and having lingual, gingival and occlusal surfaces 30, 32 and 34 respectively. The slot receives an arch wire 36 (see FIGS. 3–5, 10, 11, and 15–17), which usually in the early stages of a procedure is of circular cross section (FIGS. 3, 10, 11 and 17), and of small enough diameter for the bracket to slide freely along it once the arch wire is fully within the slot and fully aligned therein. Usually subsequently the round arch wire is replaced by one of rectangular cross section (FIG. 4) or D-shape cross section (FIG. 5) which are engaged by the spring member to give a high degree of control about the mesial distal axis for final control of tipping of the teeth into position, such engagement however causing an unavoidable increase in sliding friction resistance. Means for retaining the arch wire in the slot, and for pressing it resiliently into engagement with at least the slot lingual surface 30, and preferably also into engagement with the slot gingival surface 32, or the slot occlusal surface 34, as will be described in more detail below, comprise a self-ligating latching spring member of thin flat springy metal mounted on the bracket body in the recess that is formed between the two protruding pairs of tie wings 26.

Figure 9:
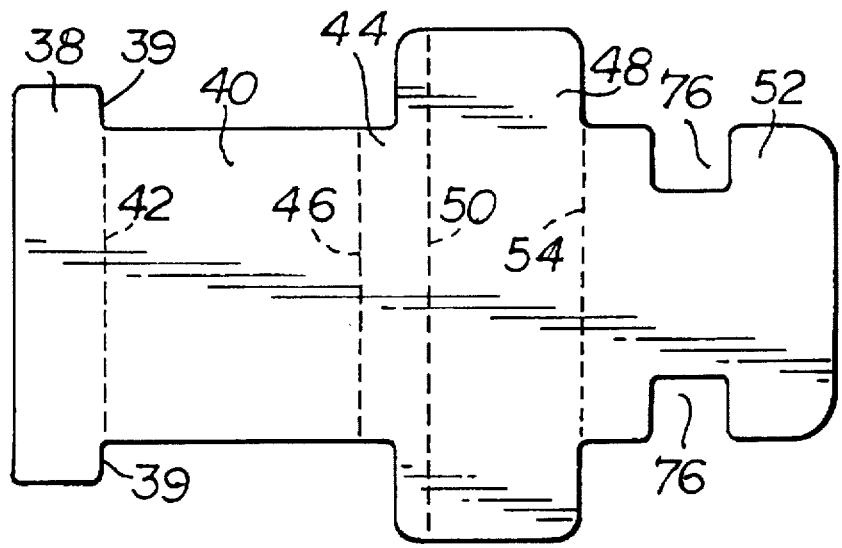
FIG. 9 is a plan view of the spring member in flattened shape prior to its conversion to either of the conformations of FIGS. 7, 8a and 8b.

For convenience in description the spring member may be regarded as comprising a number of different portions, each of which has a specific function in the overall operation of the spring member, and in the embodiment shown herein it comprises along its length in the order stated an anchor portion 38 having mesially distally extending shoulder surfaces 39, a flexing portion 40 that has a mesial distal extending junction 42 (FIG. 9) with the anchor portion, a biasing portion 44 that has a mesial distal extending junction 46 (FIG. 9) with the flexing portion, a ligating portion 48 that has a mesial distal extending junction 50 (FIG. 9) with the biasing portion, and a latching portion 52 that has a mesial distal extending junction 54 with the ligating portion.

The anchor portion 38 is wider than the flexing portion to give a T shape having mesial distal extending labial facing shoulders 39 as seen in plan (see FIG. 9) that butt against corresponding mesial distal extending lingual facing shoulders (not seen) within the body to prevent withdrawal of the spring member. Thus, the anchor portion is contained within a closely fitting slot 56 in the bracket body, the fit within the slot being so close that the portion 38 cannot flex during movement of the spring member from the slot open position shown in FIGS. 1, 10, and 12 to the latched slot closed position shown in FIGS. 2–5, 11, 13 and 15–17, and any such flexing movement can only take place in the remainder of the spring member beginning at the junction 42. The anchor portion is flat, the slot 56 is also flat and its mouth, at which any flexing movement of the spring member will start, extends the full width of the spring member. In this embodiment the slot 56 is inclined at about 45° to the occlusal surface 16 and to the labial lingual reference axis in order to preset the flexing portion 40 and determine the force required to flex the flexing portion for movement of the spring member to the slot closed position, the force being variable over a predetermined range by change of this angle.

Figure 8A:
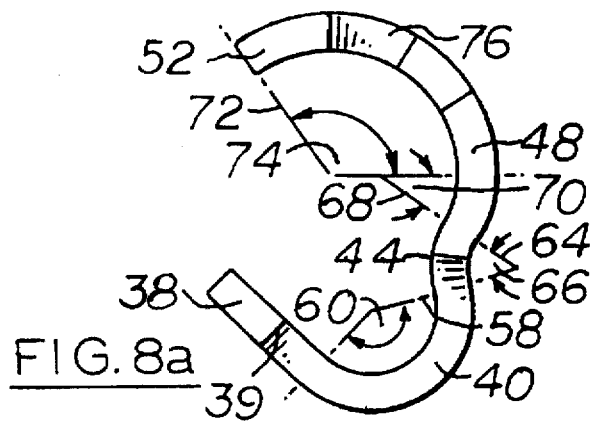
FIGS. 8a and 8b are side elevations of the spring member alone showing the radii and subtended angles of the different portions thereof respectively when in slot closed and open conformation.
Figure 8B:
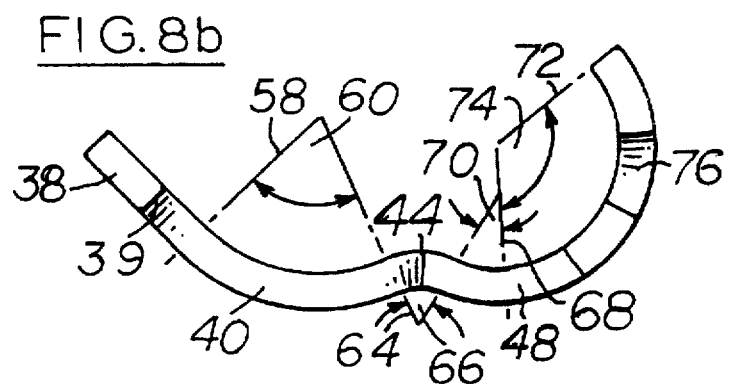

Referring now to FIGS. 8a and 8b, the flexing portion 40 is preformed to be concave toward the adjacent bracket body labial surface about a radius 58 (FIGS. 8a and 8b) and subtends an angle 60, and it is in this portion that the majority of the flexing movement takes place in movement of the spring member between the two positions, as will be described in more detail below. Some flexing will of course take place in the biasing, ligating and latching portions during these movements, that which takes place in the biasing and ligating portions depending upon the size, cross section and orientation of any arch wire in the arch wire slot 28, and that which takes place in the latching portion being necessary for the latching and unlatching. The concentration of the flexing in the flexing portion is facilitated by the fact that its mesial distal width is reduced as compared to the anchor and ligating portions, as is most clearly seen in FIG. 9. The radius 58 of the flexing portion is decreased and its subtended angle 60 is increased as the spring member moves toward the slot closed position and more and more of it butts against the adjacent smoothly curved labial surface 10 of the bracket body. In the slot closed position the flexing portion enters a slot 62 formed in the lingual surface of the bracket body, so that its edges are covered by the slot walls and cannot be engaged by the patient's tongue or inner mouth surfaces.

The biasing portion 44 is preformed to be convex toward the slot lingual wall 28 about a radius 64 and subtends an angle 66, its location along the spring member being such that in this embodiment in the slot closed position its rounded peak is at the same level as the slot occlusal surface 34 and in the absence of an arch wire in the slot the part of the portion from the rounded peak toward the gingival protrudes somewhat into the slot to provide a potential arch wire engaging surface facing toward the mesial distal extending junction of the slot lingual and gingival surfaces. The function of this portion will be described below.

A small part of the ligating portion extending from the junction 50 is formed about a radius 68 and subtends an angle 70, while the remainder of the ligating portion and the latching portion are preformed about a common radius 72 and subtend an angle 74. The ligating portion is concave toward the slot lingual wall while the latching portion is concave toward the slot gingival wall. The latching portion is also of smaller mesial distal width than the ligating portion, this facilitating its flexing for engagement and disengagement of the latches. The latching portion also enters the corresponding part of the slot 62 so that its edges are protected by the slot walls.

Figure 10:
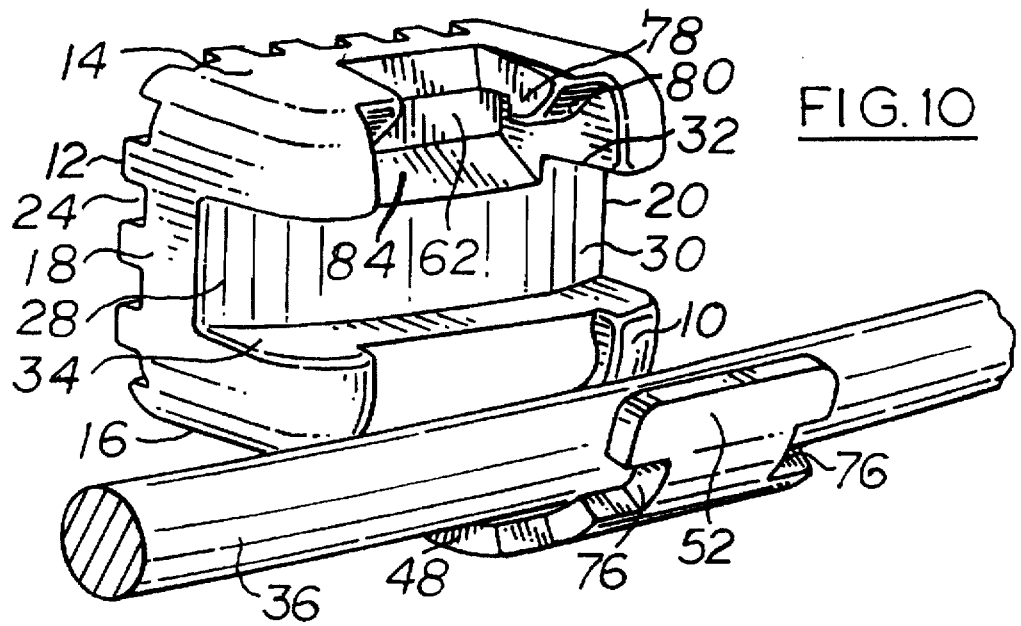
FIGS. 10 and 11 are perspective views of a wingless bracket of the invention intended particularly for lingual procedures and for attachment to upper molars, showing respectively the spring member in slot open position with a round cross section arch wire positioned on the spring member ready for insertion into the arch wire slot, and in slot closed position with the arch wire retained in the slot.

In this embodiment latching means for the required latching engagement between the latching portion 52 and the bracket body comprise two symmetrical rectangular shaped latch notches 76 respectively in the mesial and distal edges of the latching portion adjacent to its free end, the notches cooperating with registering occlusally extending latch sears 78 on the body, the sears protruding mesially and distally toward one another. While the spring member is in the unstrained slot open position shown in FIGS. 1, 10 and 12 the angle of insertion of the anchor portion in the body is not only arranged to adjust the flexing operation of the flexing portion, but is also made such that the remainder of the spring member extends labially so that the ligating portion provides a shelf or platform on which an arch wire 36 can rest, as shown in FIG. 10, and be held thereby roughly positioned ready for insertion into the slot while the wire is being latched into the first few of the brackets. The latching portion carries the arch wire with it as the spring member is flexed; subsequently the free end of the latching portion engages respective lingually occlusally inclined faces 80 of the latch sears, these faces constituting ramps producing occlusal movement of the free end until the latch sears 78 are engaged in the latch notches 76, whereupon the free end moves gingivally under the urge of the remainder of the spring member, particularly of the flexing portion, into the fully latched position. Engagement of the latches is produced by simple finger pressure against the spring member, while disengagement is produced by insertion of a suitable pointed tool 82 (FIG. 3) occlusally through the gingival opening formed by the slot 62, the tool engaging the latching portion free end and pressing it occlusally against the spring urge. The downward movement engages the free end of the spring member with a labially occlusally extending ramp surface 84 that moves the latch portion labially to ensure that the latches will become disengaged; upon disengagement the spring member immediately springs back under its own spring urge to the slot open position. The spring member receiving slot 62 is so narrow (e.g. 0.75 mm or 0.030 in) that unlatching without the use of the particular pointed tool 82 is extremely difficult, if not impossible, and in particular is not possible by use of a patient's fingernail.

Other latching means structures can also be used, for example that employed in the brackets shown and described in my U.S. Pat. No. 5,224,858, issued 6 Jul., 1993, the disclosure of which is incorporated herein by this reference. In these brackets the latch sears protrude mesially and distally toward each other instead of occlusally, and the end part of the latching portion 52 between the cooperating notches 76 would in such a structure be provided with a central slot to permit the resulting end parts to move together for engagement of the latches, and to permit disengagement of the latching sears from the notches by squeezing the end parts together, using for example a small pair of pliers.

Figure 3:
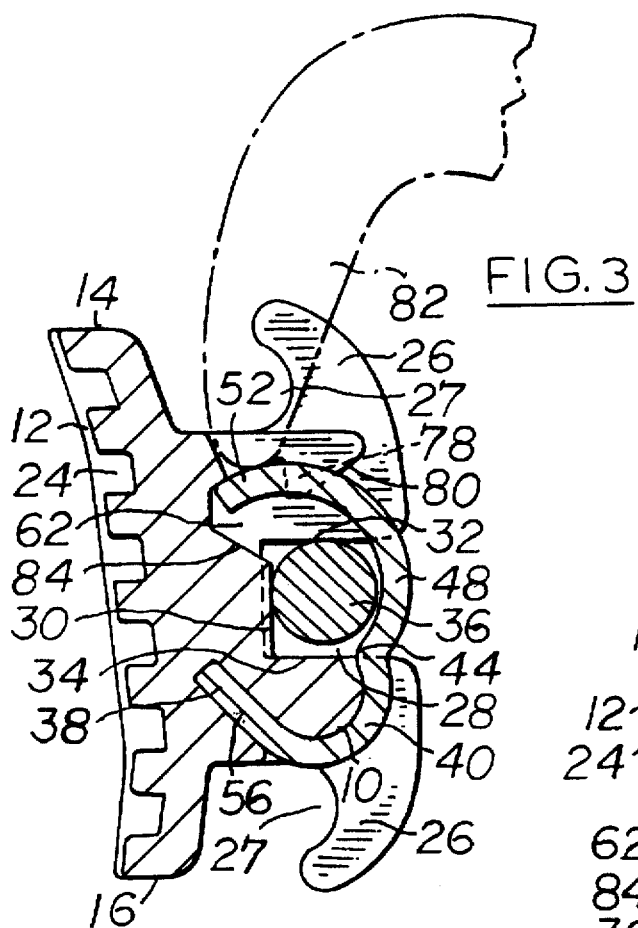
FIGS. 3 through 5 are similar cross sections in a gingival occlusal plane through a bracket of FIGS. 1 and 2 showing in the arch wire slot arch wires of respectively round, rectangular and D-shape transverse cross section.

In the initial stages of a procedure low force undersized round cross section wires, as shown in FIG. 3, or multi-strand cables such as those disclosed and claimed in my U.S. patent Ser. No. 5,334,315, issued 6 Sep., 1994, the disclosure of which is incorporated herein by this reference, usually are used that are a loose fit in the slot, so as to avoid frictional binding which can inhibit movements involved in the "unravelling" of the crowded teeth along the arch wire to their desired aligned configuration. During these early stages it is unlikely that an arch wire inserted into the slot 28 will be fully accommodated within the slot, but instead will at least attempt to protrude out of the slot mouth and/or rotate in the slot. As the spring member is moved toward the slot closed position the ligating portion 48 engages the wire and presses it into the slot, this action continuing with rotation and bending of the adjacent portions of the wire until the spring member is in the full latched slot closed position. The closing movement usually thereby stresses both the arch wire and the ligating portion, and the self-ligating spring member is able to contribute accurately and at all times to the restoring force urging the teeth to their final optimum positions.

As is most clearly seen in FIG. 3, the part of the biasing portion 44 from its junction with the ligating portion to its rounded peak effectively forms a special extension of the ligating portion that protrudes into the occlusal part of the slot and, if it engages the round cross section wire therein, urges it not only toward the slot lingual wall but also toward the junction of the lingual and gingival walls, functioning in this regard as an inclined plane along which the wire is urged to move, so that the wire is even more accurately positioned within the slot for more precise angular control than could be obtained with a ligating portion that only closes the slot mouth. Thus, with the bracket in optimum position relative to the arch wire it will slide mesially or distally on the arch wire with minimum frictional resistance and will permit only minute amounts of rotation about the labial lingual axis and/or about the occlusal gingival axis without activating the spring member to restore its position. This allows for example extremely precise control over root position and attitude as the teeth are moved to close spaces from which teeth have been extracted. The control of cross section shape obtainable in commercial practice with arch wires is much greater than the dimension control available and, for example, a wire that is nominally of 0.5 mm (0.020 in) diameter may be less by up to 0.013 mm (0.0005 in), and usually is not more. The spring member of the invention is much more tolerant of such variations in diameter by ensuring that whatever the dimension the wire will eventually always be pressed firmly into the lingual gingival slot junction, and therefore gives much more precise and predictable control of the progress of the procedure.

Figure 4:
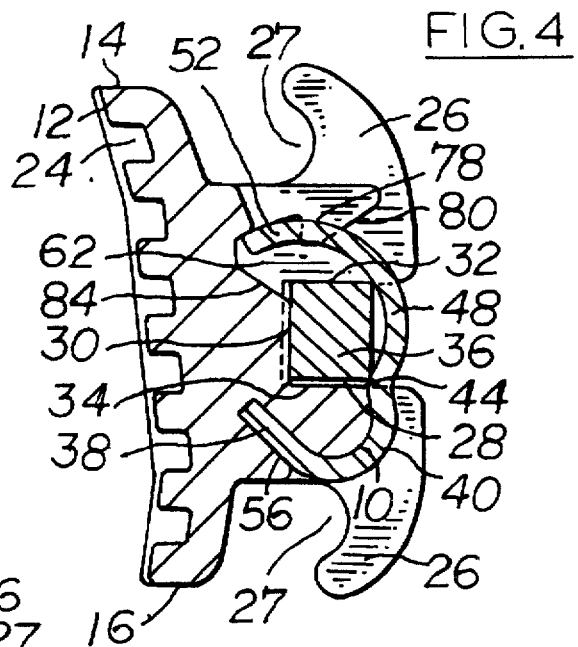
Figure 5:
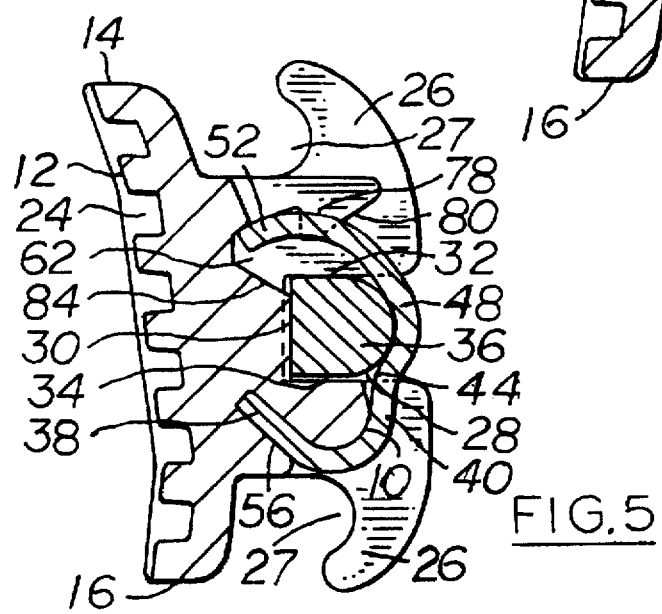

FIGS. 4 and 5 illustrate the excellent precise angular control achievable with brackets of the invention when used respectively with rectangular or D-shape arch wires 36 operating in a rectangular cross section slot. In practice, for example, a standard gingival-occlusal dimension for an arch wire slot is 0.55 mm–0.0 mm and +0.013 mm (0.022 in–0.0 in and +0.0005 in), while the largest wire used has a nominal gingival-occlusal dimension of 0.53 mm (0.021 in), but is more usually 0.52 mm (0.0205 in); wires of smaller dimension such as 0.50 mm (0.020 in) are also commonly used. As with round wires the shape control is much greater than the dimension control available and a wire that is rotationally displaced by even a very small angle is subjected to a restoring torque moment, producing the required rotation about a mesial distal axis, by the ligating portion 48 pressing the wire into the slot until the flat lingual face of the wire is butted against the lingual slot surface 30, while the biasing portion 44 is operable to press the wire gingival surface firmly against the slot gingival surface 32. A similar precise restoring effect will be produced if the protrusion of the arch wire from the slot is caused by rotational misplacement of the tooth about the gingival-occlusal axis. The concave shape of the spring member litigating portion toward the slot lingual surface makes it particularly effective when used with arch wires of D-shape cross section as shown in FIG. 5 in that the rectangular portion cooperates well with the walls of the rectangular slot while the rounded labial surface cooperates well with the butting concave surface of the litigating portion.

Figure 6:
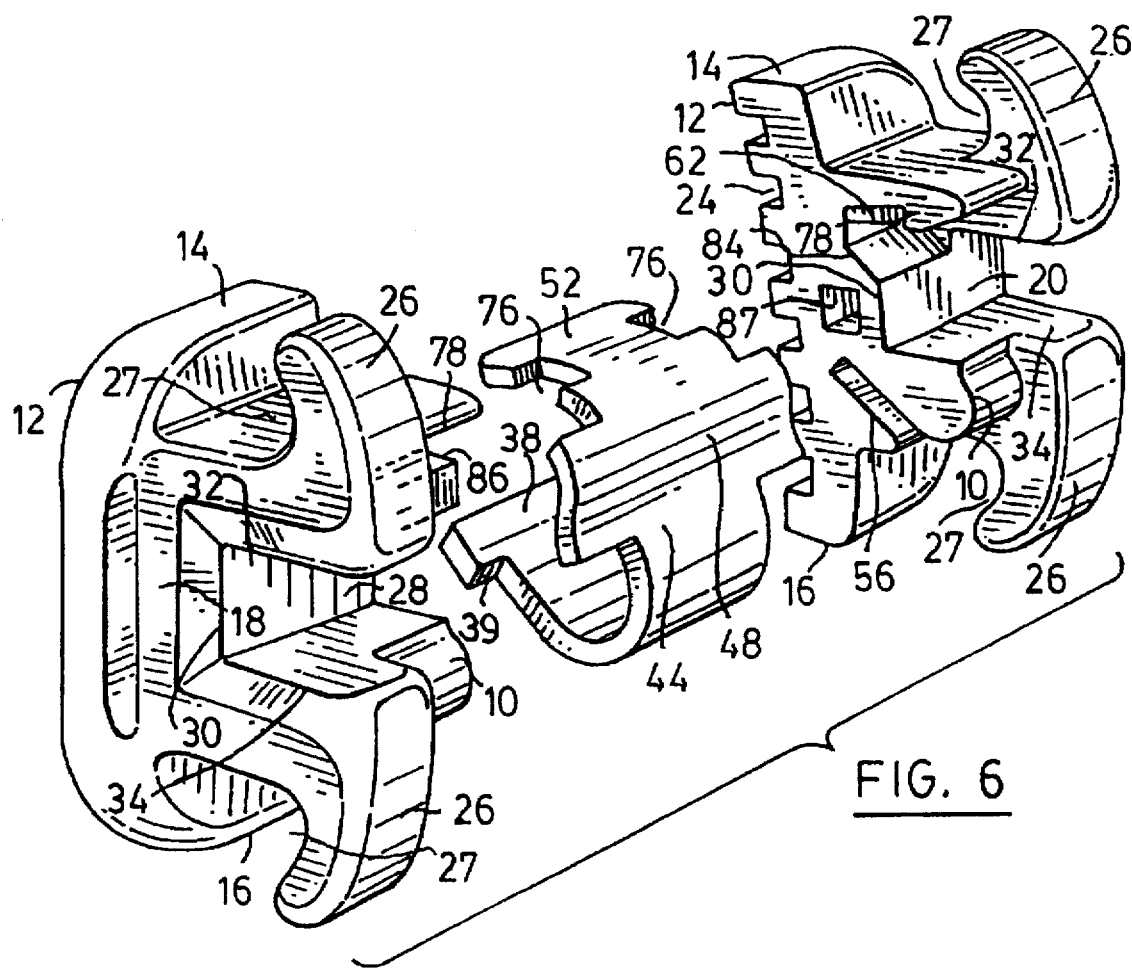
FIG. 6 is an exploded perspective view of the bracket of FIGS. 1 and 2 showing the manner in which the bracket body is made in two mirror-image parts.

FIG. 6 illustrates a simple and effective way in which the brackets of the invention can be assembled using only three parts. The bracket body is made as two mirror image parts, one of which has a mesial distal extending square cross section post 86 extending mesially or distally respectively therefrom and insertable into a registering mesial distal extending square cross section bore 87 in the other part. Upon moving the two body parts together the spring member anchor portion enters the respective parts of its retaining slot 56. The post enters the bore and ensures that the body parts are held accurately in register with one another while they are fastened together along their butting junction, as for example by laser welding, to complete the body and at the same time permanently retain the spring member in its anchor slot 56, such retention being ensured by the labial facing shoulder surfaces 39 as described above.

The bracket bodies shown herein are generally rectangular as seen from the labial or lingual, but instead they can be of rhomboidal form with the mesial and distal faces inclined at a small angle to a neutral gingival occlusal extending plane, such a bracket shape also requiring that the spring member be rhomboid in shape. This angle depends upon the corresponding inclination desired for the tooth to which the bracket is fixed, and such brackets are preferred by many orthodontists in that they facilitate the positioning of the brackets on the teeth at the start of the procedure. Thus the angle is such that with the tooth at the required angle the arch wire slot 28 extends mesially distally horizontally in the mouth in full alignment with the unstrained arch wire. The use of such rhomboid shaped brackets is now well established and well known to those skilled in the art and does not require further explanation herein.

The spring force for individual brackets may be adjusted by forming the spring members with different amounts of preloading, for example by adjustment of the angles 60, 66, 70 and 74, and also of the corresponding radii of curvature before the bracket is assembled. A continuing problem encountered with self-ligating brackets employing metal ligating springs results from the extremely small size of the brackets. Because of the requirement for high modulus metals, and the highly corrodible environment of the mouth, stainless steels have been used almost universally hitherto. Although stainless steels of the highest practical modulus are used the tiny springs are stressed very close to the elastic limit of the metal as they are moved between the slot open and closed positions, and the amount of displacement required to exceed the elastic limit is relatively small. Once that limit has been exceeded, for example by the operative carelessly moving the spring and/or attempting to force the spring to close over a stiff arch wire that protrudes too far out of the slot, then it may take such a permanent set that it can no longer function as a spring. This may require the bracket to be replaced completely, since it is not usually convenient for the orthodontist to replace the spring "in situ", especially since mounting the spring on the bracket body brings it close to the elastic limit; such replacement is of course inconvenient and unpleasant both for the patient and the orthodontist.

A new family of nickel-titanium alloys has been developed that are rapidly finding use in the fabrication of arch wires, ligating and traction springs, the most important characteristic of these alloys being their extraordinarily high elasticity with corresponding resistance to overstressing and permanent deformation, as compared to the stainless steels. FIG. 14 shows a typical stress/strain characteristic for such an alloy. Initially the stress/strain relationship is substantially linear, as with most metals, and rises relatively rapidly, but at some point, usually less than about 1% strain, they enter a superelastic phase in which the characteristic becomes almost flat, and in which the strain can increase to as high as about 6–8% without overstressing and failure to return to the unstressed shape. At the end of the superelastic phase the characteristic resumes a much steeper upward inclination. Their elasticity during the superelastic phase is such that the wires and springs made from them are not overstressed despite relatively large displacements, and can regain their original shape, when subjected to these high strains, as compared to the maximum for stainless steels of about 0.5%. For this reason they are commonly referred to as superelastic metal alloys. Another characteristic is that springs fabricated from these alloys are able to provide a relatively constant restoring force over this much wider range of deflection. The atomic structure which produces this superelasticity also causes the alloys to exhibit a so-called memory phenomenon, whereby articles made of them can be bent from a desired original "memory" shape to a new quite different shape and set in that latter shape by suitable heat treatment; subsequently if heated above a transformation temperature they will return to the original memory shape. For this reason they are also commonly referred to as superelastic shape recovery metal alloys. An example of successful products made from these alloys the multi-strand cables that are described and claimed in my U.S. Pat. No. 5,344,315, referred to above, such cables increasingly being employed to form arch wires. An arch wire of this material can be bent sufficiently to be engaged in the slots of highly relatively displaced brackets to an extent that would be impossible with stainless steels, or if possible would cause the application of dangerously high forces to the teeth and gums.

Figure 7:
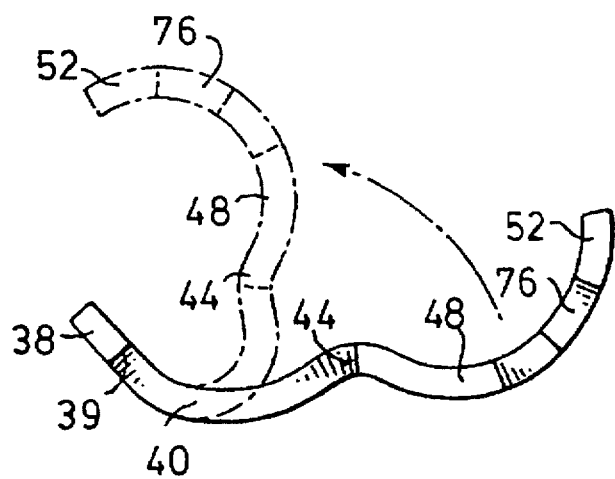
FIG. 7 is a side elevation of the spring member alone showing in solid lines its conformation in slot open position and in broken lines its conformation in slot closed position.

The properties of these alloys make them especially suited for use in the brackets of the invention, in which one end anchor portion 38 of the spring member is held firmly across its entire mesial distal width in anchor slot 56. This ensures that the initial flexing movement of the spring member, for example from slot open to closed position, will commence at the junction 42 as Hookian elastic displacement. The part of the flexing portion 40 at and close to the junction will quickly enter the superelastic phase while the remainder of the portion is still in the elastic phase, so that as will be seen by the comparison afforded by FIG. 7, the bias, ligating and latching portions tend to remain in the relative conformations that they had in the slot open position, at least during this initial movement. As the portion close to the junction reaches the end of the superelastic phase and the characteristic suddenly resumes its steeper slope, more of the flexing portion will instead enter the superelastic phase, and the transfer from elastic phase to superelastic phase will move progressively in wave-like fashion along the flexing portion. The deformation of the spring member becomes disproportionately greater where the transition from elastic to superelastic behaviour is taking place, and the effect is to confine the flexing movement required of the spring member an otherwise disproportionate amount to the flexing portion, at least until the ligating portion engages a misplaced arch wire, and until the latching portion needs to flex to engage the latches, both of which will apply significantly greater stresses to these parts of the arch wire. This ensures that the biasing, ligating and latching portions will in a large measure retain their preset shapes for as long as possible and remain in the steeper slope Hookian elastic range, rendering them correspondingly effective for their respective functions. In particular, once the spring member is fully latched, in the absence of any significant stresses imposed by the arch wire, the bias, ligating and latching portions will tend to retain their unlatched conformation, any labial displacement occurring predominantly in the flexing portion, as will be seen most clearly for example from FIG. 5, showing a D-shape cross section arch wire in the slot. Thus, in the slot closed position the flexing portion of the spring member effectively converts the open mouthed arch wire slot into mesial distal extending tube with a highly resilient labial wall and of a cross section shape such as to permit free sliding with arch wires of appropriate shape and size. Because of its lingual protrusion the bias portion 44 will tend to engage a misplaced arch wire ahead of the adjacent portions, and the arch wire forces may flatten and bulge this portion labially into the superelastic range ahead of those adjacent portions, the corresponding shape recovery augmenting the action of the arch wire by its steady application of low value forces thereto.

A preferred family of superelastic shape memory alloys is nickel/titanium, usually with a nominal atomic composition of 50%:50% nickel and titanium, but with small additions of copper, iron, cobalt or chromium, the alloy being subjected to a heat treatment to develop the desired characteristic. At this time these nickel/titanium alloys are preferred in that they have the greatest ductility, more recoverable motion, excellent corrosion resistance comparable to series 300 stainless steels, stable transformation temperatures for shape recovery, high biocompatibility, and the ability to be electrically heated for shape recovery. Other alloys are also known and are disclosed in my U.S. Pat. No. 5,344,315, referred to above, and in my application Ser. No. 08/274,077, filed Jul. 12, 1994, now U.S. Pat. No. 5,586,882, issued on 24 Dec. 1996, the disclosure of the latter also being incorporated herein by this reference.

The benefit of the greater tolerance for displacement of both the ligating and the latching portions of the spring member provided by the use of these superelastic shape memory metal alloys are such that they are to be preferred, despite their higher cost and their lower strength modulus as compared with the suitable stainless steels, so that the spring members must usually be somewhat thicker. Nevertheless stainless steel ligating latch spring members can of course also be successfully used with these new brackets.

Figure 11:
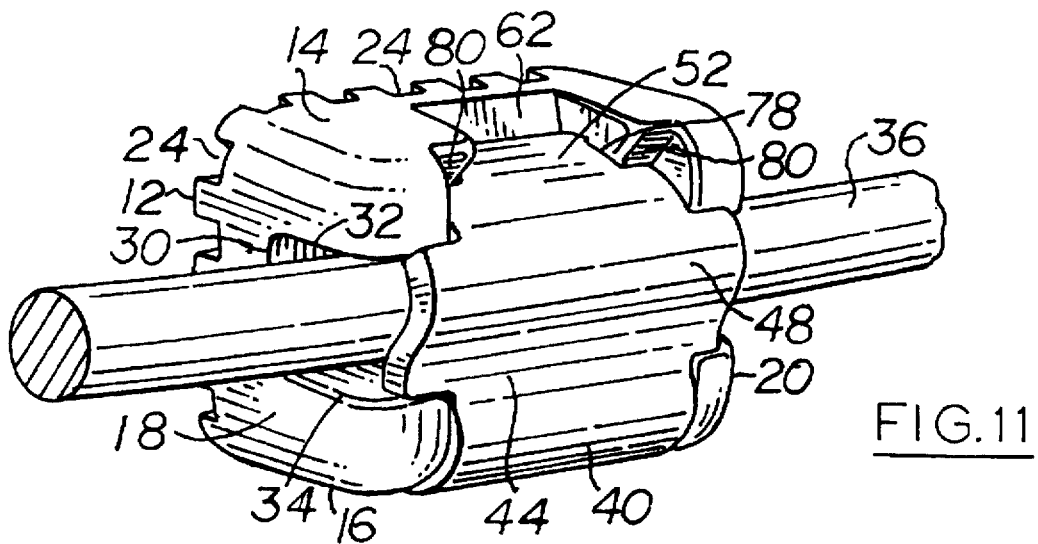

FIGS. 10 through 13 show preferred forms of the brackets of the invention intended for use with lingual procedures. In such procedures tie wings are neither practical or desired and the brackets can therefore be made even smaller than those intended for labial procedures. The bracket of FIGS. 10 and 11 is intended for application to the lingual surface of upper bicuspids and molars, while that of FIGS. 12 and 13 is intended for application to the lingual surface of upper incisors and canines. Since the desire to maintain as smooth an external contour as possible makes it impractical to provide hook or wing anchorages for other orthodontic elements, such as elastomeric loops and chains, whenever the bracket body shape is such as to permit it, as with that shown in FIG. 13, the bracket body is provided between the arch wire slot 28 and the gingival surface 14 with a second mesial distal extending slot 88, this second slot having a mesial distal extending opening 90 to the lingual surface of reduced gingival occlusal dimension through which an elastomeric orthodontic element (not shown) can be introduced into the slot and will be retained therein. Thus the elastomeric element can be a thread that is passed mesially or distally through the slot, or it can be stretched until its gingival occlusal dimension has reduced sufficiently for it to be passed through the slot mouth 90; as soon as the tension is released it will expand to fill the slot and be retained therein. In this embodiment the slot is of D shape cross section with a convex lingual surface and, in addition to elastomeric elements, can receive and utilize D shape and round cross section arch wires and auxiliaries made from D shape wire, e.g. elastic hooks.

Figure 15:
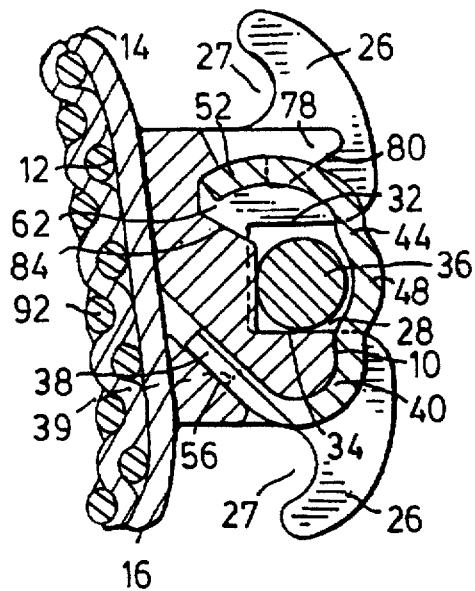
FIG. 15 is a cross section similar to FIGS. 3 through 5 showing a tie wing bracket in which the spring member has a biasing portion at the slot gingival surface.

FIG. 15 shows an alternative version of a double tie wing bracket in which the biasing portion 44 of the spring member is provided between the ligating and latching portions at the slot gingival surface, the biasing portion being convex toward the slot lingual wall and protruding into the slot so that it will urge the arch wire predominantly toward the slot lingual occlusal junction. From the point of view of obtaining more accurate control of bracket positioning by the arch wire it is immaterial whether the biasing portion is provided at the slot occlusal or gingival surface, but the spring geometry and operation is somewhat simpler when it is at the slot occlusal surface, and accordingly this is preferred. This aspect of the invention is of course applicable to both tie wing and wingless forms of the bracket. In this embodiment the lingual surface is not proved with integral grooves 24 to receive the fastening cement, but instead has welded to the lingual surface 12 a piece of stainless steel open wire mesh 92, the cement entering the open interstices of the mesh to provide the necessary increased anchorage.

Figure 16:
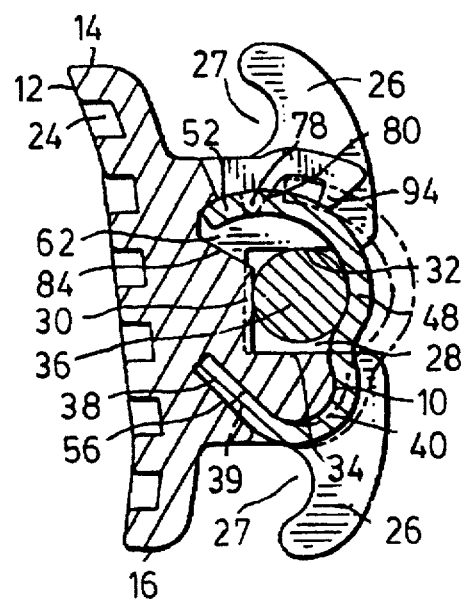
FIG. 16 is a cross section similar to FIG. 15 showing a tie wing bracket in which the spring member is latchable alternatively with two labially lingually spaced latches.

FIG. 16 shows an embodiment in which the bracket body is provided with a second pair of latch sears 94 spaced labially from the first pair 78. These labially displaced second sears allow the spring member to be latched with reduced binding, or without binding, when the arch wire slot contains a somewhat larger cross section wire, for example a rectangular edgewise wire of dimensions 0.525 mm×0.625 mm (0.021 in×0.025 in), and/or when the arch wire is slightly displaced and would otherwise frictionally engage a part of the spring member. At any time the spring member can be moved by finger pressure to the first pair of latches.

Figure 17:
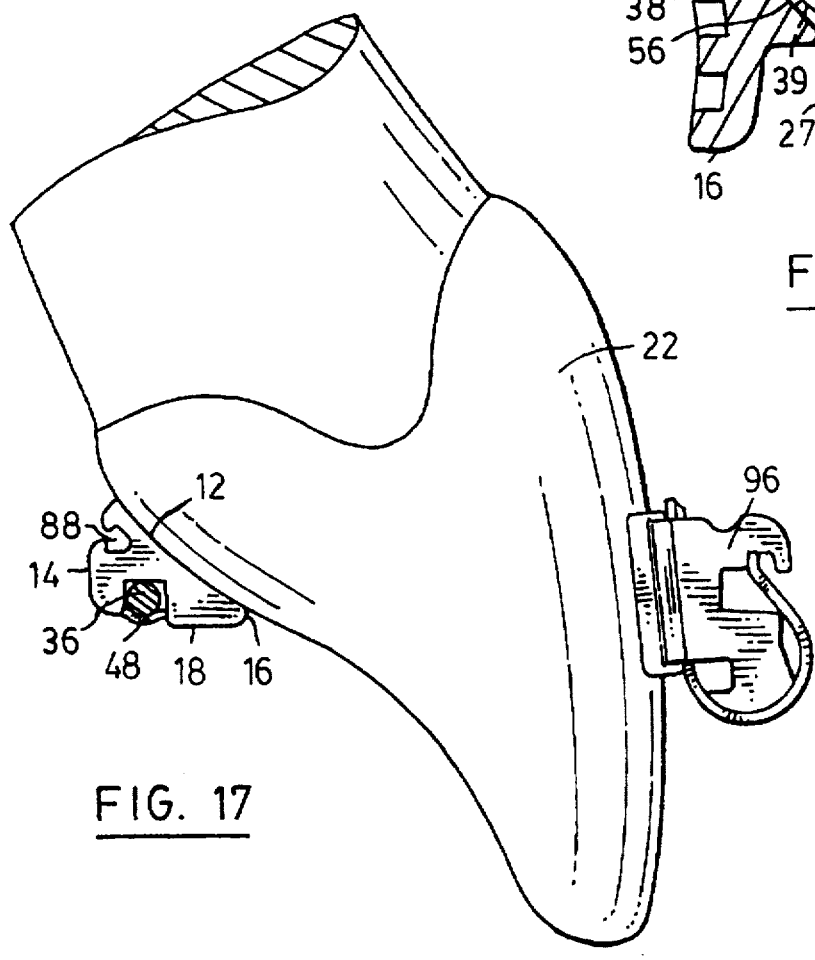
FIG. 17 is an outline of an adult central incisor tooth having a bracket of the invention cemented to the lingual surface thereof, and for comparison in size a bracket of the Hanson SPEED System cemented to the labial surface.

FIG. 17 illustrates and emphasises the small size to which it is possible to make the brackets of the invention, as compared to the size of a typical adult tooth 22 to which the bracket is attached, and as compared to a typical Hanson SPEED system bracket 96 shown cemented to the labial tooth surface. Typically one of these prior art brackets currently in use has a body that measures 2.7 mm to 3.0 mm (0.108 in to 0.130 in) in gingival occlusal height, 2.7 mm to 3.0 mm (0.108 in to 0.130 in) in its widest mesial distal width adjacent to the lingual body surface, and 2.1 mm to 2.7 mm (0.094 in to 0.108 in) in labial lingual depth. The spring ligating member is of stainless steel of about $28-29 \times 10^6$ psi elastic modulus (which is a measure of its stiffness), and measures 0.125 mm (0.005 in) in thickness and 1.57 mm to 1.83 mm (0.062 in to 0.072 in) in the mesial distal dimension. Because of the presence of the tie wings a winged bracket of the invention measures about the same as the prior art bracket in gingival occlusal height and mesial distal width, but can be as small as 1.6 mm (0.064 in) in labial lingual thickness. A wingless bracket of the invention can be much smaller and a particular embodiment measures 1.5 mm (0.060 in) in gingival occlusal height, as low as 1.05 mm (0.042 in) in labial lingual thickness, and 2.0 mm (0.08 in) in mesial distal width. The spring member is of a nickel/titanium superelastic shape memory alloy of about $10 \times 10^6$ psi elastic modulus at body temperature (38.5° C.), the alloys being somewhat temperature sensitive and, for example, the modulus of this particular alloy drops to about $7 \times 10^6$ psi at a temperature of 21.3° C.). As seen flat in FIG. 9 the spring member measures 0.127 mm to 0.178 mm (0.005 in to 0.007 in) in thickness, 1.4 mm (0.056 in) in the mesial distal width dimension at the anchor portion 38; 1.125 mm (0.045 in) in the mesial distal dimension at the flexing and latching portions 40 and 52; and 1.8 mm (0.072 in) in the mesial distal dimension at the litigating portion 48.

I claim:

1. An orthodontic bracket comprising:

a bracket body having labial, lingual, gingival, occlusal, mesial and distal surface portions, the body having therein a mesial distal extending arch wire slot having lingual, gingival, and occlusal surfaces and opening to the bracket lingual surface portion; and a ligating latch spring member having the form of a thin flat metal strip and comprising along its length in the order stated an anchor portion, a flexing portion, a ligating portion and a latching portion;

the spring member also comprising a biasing portion between the flexing and ligating portions at the slot occlusal surface, or between the ligating and latching portions at the slot gingival surface, the biasing portion being convex toward the slot lingual surface and protruding into the slot;

wherein the anchor portion is retained by the bracket body to retain the spring member on the bracket body;

the ligating and latching portions are movable by flexing of the flexing portion between a slot open position in which the slot opening is open for insertion of an arch wire into the slot, and a latched slot closed position in which the slot opening is closed by the ligating portion for retention thereby of an arch wire in the slot; and the spring member is latched in the slot closed position by latching engagement between the latching portion and the bracket body.

2. A bracket as claimed in claim 1, wherein the shape of the spring member in the unstrained slot open position and its insertion in the body is such that in the slot open position it extends labially to provide a platform on which an arch wire can rest during the course of a procedure.

3. A bracket as claimed in claim 1, wherein the bracket body is provided between the arch wire slot and the gingival surface with a second mesial distal extending slot, the second slot having a mesial distal extending opening to the lingual surface of reduced gingival occlusal dimension through which an elastomeric orthodontic element can be introduced into the slot and will be retained therein.

4. A bracket as claimed in claim 1, wherein the spring member ligating portion is concave toward the slot lingual wall.

5. A bracket as claimed in claim 1, wherein the spring member is made of a shape memory metal.

6. A bracket as claimed in claim 5, wherein the spring member is made of a nickel titanium shape memory alloy.

7. A bracket as claimed in claim 1, wherein the bracket body has two pairs of tie wings for the reception and retention of an external ligature, the two pairs being spaced mesially distally from one another, and the two wings of each pair extending gingivally and occlusally away from one another; and wherein the spring member is disposed on the body between the tie wings.

8. A bracket as claimed in claim 1, wherein the bracket body is made as two mirror image parts which butt one another at a junction, and between which the ligating latch spring member is mounted, the two body parts being fastened together at their junction to retain the spring member thereon.

9. A bracket as claimed in claim 1, wherein the flexing portion is of smaller width in the mesial distal direction than the anchor and ligating portions, whereby the flexibility of the flexing portion is greater than that of the anchor and ligating portions.

10. A bracket as claimed in claim 1, wherein means for effecting latching engagement between the spring member latching portion and the bracket body comprises a pair of notches in the mesial and distal edges of the latching portion adjacent to its free end, and cooperating occlusally extending latch sears on the bracket body which engage in the respective notch to effect the latching, and wherein there are provided two labially spaced pairs of latch sears, each pair of sears being alternatively engageable with the latch notches.

11. An orthodontic bracket comprising:

a bracket body having labial, lingual, gingival, occlusal, mesial and distal surface portions, the body having therein a mesial distal extending arch wire slot having lingual, gingival, and occlusal surfaces and opening to the bracket lingual surface portion; and a ligating latch spring member having the form of a thin flat metal strip and comprising along its length in the order stated an anchor portion, a flexing portion, a ligating portion and a latching portion;

the spring member having the anchor portion inserted within a close fitting slot in the bracket body to retain the spring member on the bracket body, and the ligating and latching portions being movable by flexing of the flexing portion between a slot open position in which the slot opening is open for insertion of an arch wire into the slot, and a latched slot closed position in which the slot opening is closed by the ligating portion for retention thereby of an arch wire in the slot;

the spring member being latched in the slot closed position by latching engagement between the latching portion and the bracket body.

12. A bracket as claimed in claim 11, wherein the spring member also comprises a biasing portion between the flexing and ligating portions at the slot occlusal surface, or between the ligating and latching portions at the slot gingival surface, the biasing portion being convex toward the slot lingual surface and protruding into the slot.

13. A bracket as claimed in claim 11, wherein the shape of the spring member in the unstrained slot open position and its insertion in the body is such that in the slot open position it extends labially to provide a platform on which an arch wire can rest during the course of a procedure.

14. A bracket as claimed in claim 11, wherein the bracket body is provided between the arch wire slot and the gingival surface with a second mesial distal extending slot, the second slot having a mesial distal extending opening to the lingual surface of reduced gingival occlusal dimension through which an elastomeric orthodontic element can be introduced into the slot and will be retained therein.

15. A bracket as claimed in claim 11, wherein the spring member ligating portion is concave toward the slot lingual wall.

16. A bracket as claimed in claim 11, wherein the spring member is made of a shape memory metal.

17. A bracket as claimed in claim 16, wherein the spring member is made of a nickel titanium shape memory alloy.

18. A bracket as claimed in claim 11, wherein the bracket body has two pairs of tie wings for the reception and retention of an external ligature, the two pairs being spaced mesially distally from one another, and the two wings of each pair extending gingivally and occlusally away from one another; and wherein the spring member is disposed on the body between the tie wings.

19. A bracket as claimed in claim 11, wherein the bracket body is made as two mirror image parts which butt one another at a junction, and between which the ligating latch spring member is mounted, the two body parts being fastened together at their junction to retain the spring member thereon.

20. A bracket as claimed in claim 11, wherein the flexing portion is of smaller width in the mesial distal direction than the anchor and ligating portions, whereby the flexibility of the flexing portion is greater than that of the anchor and ligating portions.

21. A bracket as claimed in claim 11, wherein means for effecting latching engagement between the spring member latching portion and the bracket body comprises a pair of notches in the mesial and distal edges of the latching portion adjacent to its free end, and cooperating occlusally extending latch sears on the bracket body which engage in the respective notch to effect the latching, and wherein there are provided two labially spaced pairs of latch sears, each pair of sears being alternatively engageable with the latch notches.

* * * * *